US00PP08669P

United States Patent [19]

Trees

[11] Patent Number: Plant 8,669

[45] Date of Patent: Mar. 29, 1994

[54] GERANIUM PLANT 'DESIGNER SCARLET'

[75] Inventor: Scott C. Trees, Nipomo, Calif.

[73] Assignee: Ball Floraplant, A Division of Geo. J. Ball, Inc., West Chicago, Ill.

[21] Appl. No.: 996,113

[22] Filed: Dec. 23, 1992

[51] Int. Cl.[5] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Arnold, White & Durkee

[57] ABSTRACT

Geranium Designer Series TM Scarlet (BFP-27) is a new and distinct cultivar of geranium, botanically known as *Pelargonium*×*hortorum* Bailey, and hereinafter referred to by the cultivar name Designer Scarlet. Designer Scarlet was selected from a hybridization between female parent 7GRT-124B and male parent Tango. The new cultivar is distinguished from other geraniums and both parents by its orange scarlet color and its good basal branching in the absence of a growth regulator.

1 Drawing Sheet

BACKGROUND OF THE NEW PLANT

Designer Scarlet is a product of a planned breeding program which had the objective of creating new geranium cultivars with medium green foliage, self branching habit, non-growth regulator requiring, high productivity, uniformity among colorform, fast rooting with exceptional weather tolerance and landscape performance.

Designer Scarlet was originated from a hybridization made in a controlled breeding program in West Chicago, Ill. The female parent was 7GRT-124B, a plant with a single, salmon-coral with freckle flower and medium green foliage with light zone. 7-GRT-124B is a proprietary breeding line not commercially available. It is maintained solely for breeding purposes. 7GRT-124B has relatively good branching (2.0–2.5 branches/10 cm pot). Designer Scarlet displays 1.5–2.5 branches in a 10 cm pot. The male parent of BFP-27 was Tango (U.S. Plant. Pat. No. 5,933), a dark foliaged, compact plant with bright red flowers. Tango maintains stable chlorophyll during shipping.

Designer Scarlet is easily distinguished in appearance from the pollen parent Tango. Designer Scarlet has medium to light green foliage (137A, 137B) whereas Tango has dark green foliage (136A,136B), Tango exhibits branching of 1.0–2.0 branches in a 10 cm pot compared to 1.5–2.5 branches for Designer Scarlet.

Designer Scarlet was discovered and selected as one flowering plant within the progeny of the stated cross by the inventor in a controlled environment in Santa Maria, Calif.

The first act of asexual reproduction of Designer Scarlet was accomplished when vegetative cuttings were taken from the initial selection in a controlled environment in Santa Maria, Calif. by a technician supervised by the inventor. Horticultural examination of selected units demonstrated that the combination of characteristics as herein disclosed for Designer Scarlet are firmly fixed and are retained through successive generations of asexual reproduction.

Designer Scarlet has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

The following traits have been repeatedly observed and are determined to be basic characteristics of Designer Scarlet which in combination distinguish this geranium as a new and distinct cultivar. These traits include basal branching without growth regulators, a clean peduncle, and an orange scarlet semi-double form with petaloids.

Of the many commercial cultivars known to the present inventor, the most similar in comparison to Designer Scarlet is Red Satisfaction (U.S. Plant Pat. No. 7,641). Designer Scarlet and Red Satisfaction have a similar orange scarlet color although general tonality is somewhat different. Both plants have non-imbricate petals and produce approximately the same number of flowers/umbel. Red Satisfaction has weak peduncles due to a vestigial node which causes flowers to lodge during wind and rain. In contrast, Designer Scarlet is more wind and rain tolerant because of its stronger peduncle and lack of vestigial node. The BFP-27 plant is also somewhat shorter and narrower than Red Satisfaction.

Designer Scarlet has 1–3 petaloids 1.8–2.2 cm long and 0.5–1.0 cm wide compared with 3–5 petaloids 1.5–2.0 cm long and 0.2–0.7 cm wide for Red Satisfaction. The petals and petaloids of Designer Scarlet are broader and flatter than those of Red Satisfaction.

DESCRIPTION OF THE PHOTOGRAPH

The accompanying color photographs show a top view of typical flower and foliage characteristics of Designer Scarlet. The view taken against a dark background illustrates flower color closest to the color values assigned from The Royal Horticultural Society Color Chart. The view taken against a light background highlights the leaf characteristics.

DESCRIPTION OF THE PLANT

In the following description, color references are made to The Royal Horticultural Society Color Chart. The color values were determined between 10:00–11:00 a.m. on Nov. 9, 1992 under 500 foot candles at Arroyo Grande, Calif. USA.

Classification:

*Botanical.*—*Pelargonium* × *hortorum* Bailey.
*Commercial.*—Designer Scarlet.

INFLORESCENCE

Umbel:
- *Average diameter.*—9.5–10.0 cm.
- *Average depth.*—7.5–8.0 cm.
- *Peduncle length.*—15.5–16 cm.
- *Pedicel length.*—31–33 cm.
- *Number umbels/plant (designate circumstances).*—10–11 on field grown plants 18 weeks old.
- *Number of flowers/umbel.*—28.

Corolla:
- *Petals.*—Length: 2.5–3.0 cm. Width: 2.2–2.5 cm.
- *No. of petals.*—5–6.
- *Petal color.*—Orange-scarlet (40A) Base of each two upper petals on each floret has an additional small blotch of Red Group 52A as well as Red Group 52D giving the petal a noticeable "freckle" or "eye" on two of the 5 petals which make up the floret.
- *Appearance.*—The petal attachment point on the back of each petal is distinctly white and forms an overall star-like pattern as the five petals merge together at the calyx.
- *Average diameter.*—4.2–4.5 cm.
- *Form.*—Semi-double with petaloids.
- *Number of petaloids.*—1–3.
- *Color (general tonality from a distance of three meters).*—Orange Scarlet 40A.
- *Description of petal form.*—Non-imbricate.
- *Color (abaxial).*—40A.
- *Color (adaxial).*—40C.

Bud:
- *Shape.*—Round-oval.
- *Color (abaxial).*—40A.
- *Color (adaxial).*—40B.

Reproductive organs:
- *Androecium.*—Six 7–8 mm. anther/filaments. 1.9–2 mm anther. 33A (pollen).
- *Gynoecium.*—6–6.5 mm, 5 lobed stigma, 3 mm style.
- *Presence or absence of fruits.*—Occasionally sets fruit in greenhouse and field.

Spring flowering response period: 7 weeks from rooted cuttings grown in Arroyo Grande, Calif. 60 degree nights. 72 degree days.

Outdoor flower production: 9–11 umbels on 18 week old plants.

Durability: The clean peduncle of Designer Scarlet allows more resistance to wind and rain than comparable plants such as Red Satisfaction which often maintains a vestigial node near the base which weakens the flowering umbel during windy weather.

Peduncles:
- *Length.*—15.5–16.0 cm. (Compare Red Satisfaction: 13.5–14.0 cm).

Foliage:
- *Size.*—10.0–11.0 cm at widest point. 5.5–6.0 cm at narrowest point.
- *Leaf stem (pedicel).*—5.7–7.0 cm.
- *Form.*—Reniform, cordate.
- *Margin.*—Crenate.
- *Color (abaxial).*—137A leaf margin. 137B leaf base.
- *Color (adaxial).*—138A. 146C — veins.
- *Color (zonation).*—Slight.
- *Tolerance of botrytis.*—None claimed.

General appearance and form:
- *Internode length.*—2.5–2.7 cm.
- *Branching pattern.*—Basal branching.
- *Height.*—24.3 cm on 10 week pot grown in greenhouse.
- *Basal branching.*—Pinching not required to obtain basal branching.
- *No. of branches.*—1.5–2.5 branches in a 10 cm pot.

What is claimed is:

1. A new and distinct geranium cultivar, substantially as herein described and shown, characterized by its orange-scarlet color, strong peduncle and basal branching in the absence of growth regulators.

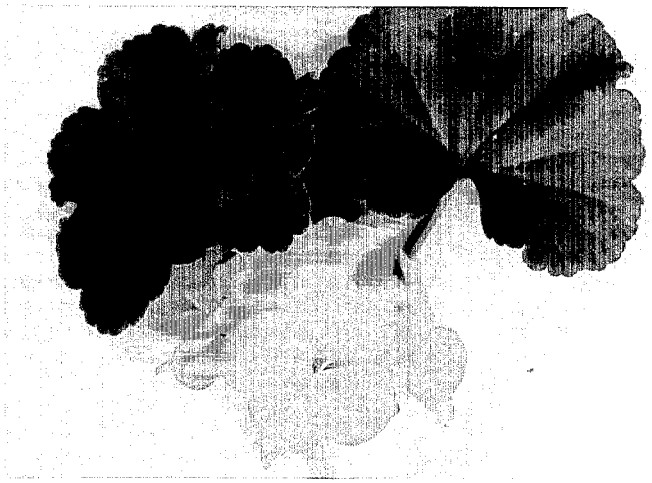
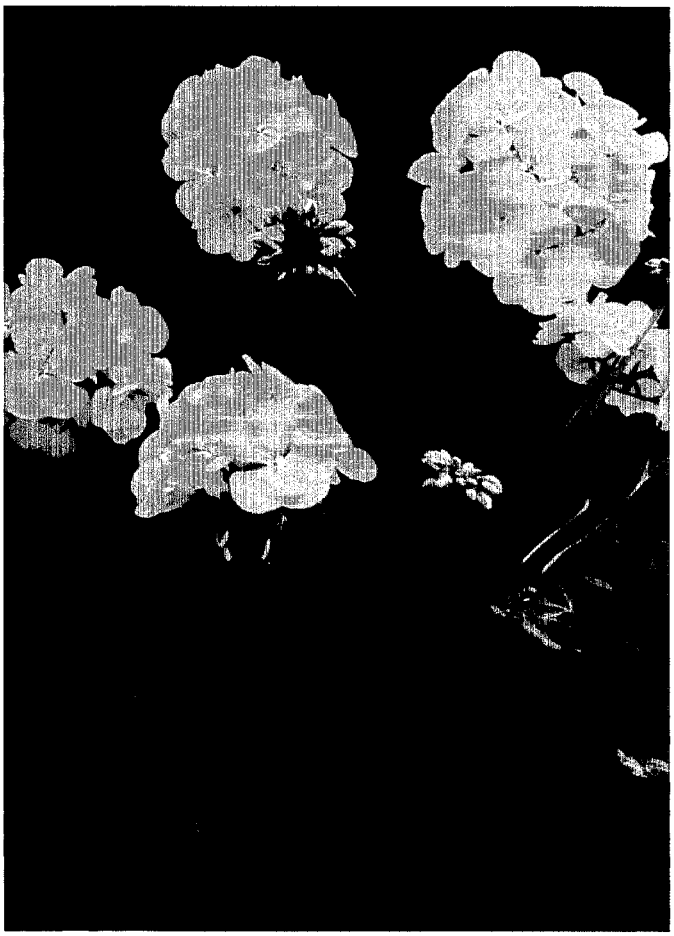

* * * * *